United States Patent
Yu et al.

(10) Patent No.: US 8,271,084 B2
(45) Date of Patent: Sep. 18, 2012

(54) DETERMINATION OF STIMULATION DELAY BETWEEN VENTRICULAR SITES

(75) Inventors: Yinghong Yu, Shoreview, MN (US); Jiang Ding, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 809 days.

(21) Appl. No.: 12/259,055

(22) Filed: Oct. 27, 2008

(65) Prior Publication Data

US 2009/0112276 A1      Apr. 30, 2009

Related U.S. Application Data

(60) Provisional application No. 60/983,548, filed on Oct. 29, 2007.

(51) Int. Cl.
 *A61N 1/368* (2006.01)
(52) U.S. Cl. .............................. 607/9; 607/42; 607/148
(58) Field of Classification Search .............. 607/9, 17, 607/25, 30, 42, 148
See application file for complete search history.

(56) References Cited

U.S. PATENT DOCUMENTS

| | | | |
|---|---|---|---|
| 7,013,176 B2 | 3/2006 | Ding et al. | |
| 7,123,960 B2 | 10/2006 | Ding et al. | |
| 7,181,285 B2 | 2/2007 | Lindh et al. | |
| 7,203,540 B2 | 4/2007 | Ding et al. | |
| 2004/0019365 A1 | 1/2004 | Ding et al. | |
| 2004/0193223 A1 | 9/2004 | Kramer et al. | |
| 2005/0137630 A1 | 6/2005 | Ding et al. | |
| 2006/0047320 A1 | 3/2006 | Ding et al. | |
| 2006/0241703 A1 | 10/2006 | Ding et al. | |
| 2007/0150013 A1* | 6/2007 | Ding et al. | 607/9 |

OTHER PUBLICATIONS

"International Application Serial No. PCT/US2008/012180, International Search Report mailed Feb. 18, 2009", 7 pgs.
"International Application Serial No. PCT/US2008/012180, Written Opinion mailed Feb. 18, 2009", 8 pgs.
"Japanese Application Serial No. 2010-532027, Office Action mailed May 15, 2012", (w/English Translation), 4 pgs.

* cited by examiner

*Primary Examiner* — Rex R Holmes
(74) *Attorney, Agent, or Firm* — Schwegman, Lundberg & Woessner, P.A.

(57) ABSTRACT

An earlier intrinsic activation and a later intrinsic activation of a right ventricle and a left ventricle are determined. This information is used for computing a biventricular pacing interval as a function of an interval from a pacing energy delivered to a ventricle corresponding to the later intrinsic activation and a depolarization sensed in a ventricle having earlier intrinsic activation, the depolarization evoked in response to the pacing energy.

25 Claims, 4 Drawing Sheets

DETERMINATION OF STIMULATION DELAY BETWEEN VENTRICULAR SITES

CROSS-REFERENCE TO RELATED APPLICATION

This application claims the benefit of U.S. Provisional Application No. 60/983,548, filed on Oct. 29, 2007, under 35 U.S.C. §119(e), which is hereby incorporated by reference.

TECHNICAL FIELD

This document pertains generally to cardiac therapy, and more particularly, but not by way of limitation, to determining a stimulation delay between ventricular sites.

BACKGROUND

Cardiac rhythm management devices include implantable devices that provide electrical stimulation to selected chambers of the heart in order to treat disorders of cardiac rhythm. A pacemaker is a cardiac rhythm management device that paces the heart with timed pacing pulses. The most common condition for which pacemakers are used is in the treatment of bradycardia, where the ventricular rate is too slow. Intermittent or permanent atrio-ventricular conduction defects (e.g., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate or artificially restoring AV conduction.

Pacing therapy can also be used in the treatment of heart failure, which refers to a clinical syndrome in which an abnormality of cardiac function causes a below normal cardiac output that can fall below a level adequate to meet the metabolic demand of peripheral tissues. Heart failure can be caused by a variety of reasons, ischemic heart disease being the most common. Some heart failure subjects suffer from intraventricular or interventricular conduction defects (e.g., bundle branch blocks) such that their cardiac outputs can be increased by improving the synchronization of ventricular contractions with electrical stimulation. In order to treat these problems, implantable cardiac devices have been developed that provide appropriately timed electrical stimulation to one or more heart chambers in an attempt to improve the coordination of atrial or ventricular contractions, sometimes termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output.

OVERVIEW

CRT can apply stimulation pulses to both ventricles, either simultaneously or separated by a specified biventricular offset (BVO) interval, and after a specified atrio-ventricular delay (AVD) interval with respect to the detection of an intrinsic atrial contraction or an atrial pace. Appropriate specification of these pacing parameters is helpful in order to achieve desired improvement in cardiac function.

Example 1 describes a system. In this example, the system comprises a right ventricular sensing channel configured to sense a right ventricular intrinsic activation. In this example, the system also comprises a left ventricular sensing channel configured to sense a left ventricular intrinsic activation. In this example, the system also comprises a right ventricular pacing channel configured to deliver a pacing energy to a right ventricle. In this example, the system also comprises a left ventricular pacing channel configured to deliver a pacing energy to a left ventricle. In this example, the system also comprises an implantable or external processor, communicatively coupled to the right and left ventricular sensing and pacing channels, wherein the processor is configured to determine an earlier activation and a later activation of the right ventricle and the left ventricle intrinsic activations during a first cardiac cycle using information about the sensed right and left ventricular intrinsic activations, to trigger a first pacing energy to a ventricle corresponding to the later activation during a second cardiac cycle, to receive an indication of a first depolarization in a ventricle corresponding to the earlier activation, the first depolarization being evoked in response to the first pacing energy, to measure a first interval ($\beta$) from a time of the first pacing energy to a time of the first depolarization, and to compute a first biventricular pacing interval between left and right ventricular paces, a first biventricular offset (BVO) interval, as a function of the first interval $\beta$.

In Example 2, the system of Example 1 optionally comprises the processor being configured to trigger the first pacing energy at a specified atrio-ventricular delay (AVD) after a right atrial event.

In Example 3, the system of any one or more of Examples 1-2 is optionally configured such that the processor is configured to compute the first BVO interval as:

$$BVO = k_1(\beta)$$

wherein $0 \leq |k_1| \leq 1$.

In Example 4, the system of any one or more of Examples 1-3 is optionally configured such that $k_1$ is 0.5.

In Example 5, the system of any one or more of Examples 1-4 optionally comprises the processor being configured to compute the first BVO interval as:

$$BVO = k_2(\beta) + k_3$$

wherein the coefficients $k_2$ and $k_3$ are derived from an analysis of clinical population data relating measured $\beta$ to a desired BVO interval for delivering cardiac resynchronization therapy, wherein the desired BVO interval is determined by a measurement of a cardiac function parameter.

In Example 6, the system of any one or more of Examples 1-5 optionally comprises an atrial sensing channel configured to sense an atrial event, and wherein the processor is configured to measure an intrinsic atrio-ventricular interval $AV_R$ using the sensed atrial event and the sensed right ventricular intrinsic activation, to measure an intrinsic atrio-ventricular interval $AV_L$ using the sensed atrial event and the sensed left ventricular intrinsic activation, and to compute a second BVO interval as a function of the $AV_R$ and the $AV_L$.

In Example 7, the system of any one or more of Examples 1-6 optionally comprises the processor being configured to compute the second BVO interval as $BVO = k_4(AV_R) + k_5(AV_L) + k_6$, wherein the coefficients $k_4$, $k_5$, and $k_6$ are derived from an analysis of clinical population data relating measured $AV_R$ and $AV_L$ to a desired BVO interval for delivering cardiac resynchronization therapy, and wherein the desired BVO interval is determined by a measurement of a cardiac function parameter.

In Example 8, the system of any one or more of Examples 1-7 optionally comprises the processor being configured to compute the second BVO interval as: $BVO = k_7(\Delta_{RL}) + k_8$, wherein $\Delta_{RL}$ is the difference between the $AV_R$ and the $AV_L$, wherein the coefficients $k_7$ and $k_8$ are derived from an analysis of clinical population data relating measured $\Delta_{RL}$ to a desired BVO interval for delivering cardiac resynchronization therapy, and wherein the desired BVO interval is determined by a measurement of a cardiac function parameter.

In Example 9, the system of any one or more of Examples 1-8 optionally comprises the process being configured to set a BVO interval using at least one of the first BVO interval or the second BVO interval.

In Example 10, the system of any one of more of Examples 1-9 optionally comprises the processor being configured to set a BVO interval as a function of the first BVO and the second BVO.

In Example 11, the system of any one or more of Examples 1-10 optionally comprises the processor being configured to set the BVO interval as $BVO = k_9(\beta) + k_{10}(AV_R) + k_{11}(AV_L) + k_{12}$, wherein the coefficients $k_9$, $k_{10}$, $k_{11}$, and $k_{12}$ are derived from an analysis of clinical population data relating measured $\beta$, $AV_R$, and $AV_L$ to a desired BVO interval for delivering cardiac resynchronization therapy, and wherein the desired BVO interval is determined by a measurement of a cardiac function parameter.

In Example 12, the system of any one or more of Examples 1-11 optionally comprises the processor being configured to set the BVO interval as $BVO = k_{13}(\beta) + k_{14}(\Delta_{RL}) + k_{15}$, wherein the coefficients $k_{13}$, $k_{14}$, and $k_{15}$ are derived from an analysis of clinical population data relating measured $\beta$ and $\Delta_{RL}$ to a desired BVO interval for delivering cardiac resynchronization therapy, and wherein the desired BVO interval is determined by a measurement of a cardiac function parameter.

In Example 13, the system of any one or more of Examples 1-12 optionally comprises the processor being configured to set the BVO interval by selecting between the first BVO interval and the second BVO interval.

Example 14 describes a method for setting desired pacing parameters for delivering cardiac resynchronization therapy to a subject, including sensing a right ventricular intrinsic activation, sensing a left ventricular intrinsic activation, determining an earlier activation and a later activation of the right ventricle and the left ventricle intrinsic activations during a first cardiac cycle using information about the sensed right and left ventricular intrinsic activations, delivering a first pacing energy to a ventricle corresponding to the later activation during a second cardiac cycle, sensing a first depolarization in a ventricle corresponding to the earlier activation, the first depolarization being evoked in response to the first pacing energy, measuring a first interval ($\beta$) from a time of the first pacing energy to a time of the first depolarization; and computing a first biventricular pacing interval between left and right ventricular paces, a first biventricular offset (BVO) interval, as a function of the first interval $\beta$.

In Example 15, the method of Example 14 is optionally performed such that the delivering the first pacing energy includes delivering at a predetermined desired atrio-ventricular delay (AVD) after a right atrial event.

In Example 16, the method of any one or more of Examples 14-15 is optionally performed such that the computing the first BVO interval includes as: $BVO = k_1(\beta)$, wherein $0 \leq |k_1| \leq 1$.

In Example 17, the method of any one or more of Examples 14-16 is optionally performed such that $k_1$ is 0.5.

In Example 18, the method of any one of more of Examples 14-17 is optionally performed such that the computing the first BVO interval includes as: $BVO = k_2(\beta) + k_3$, and wherein the coefficients $k_2$ and $k_3$ are derived from an analysis of clinical population data relating measured $\beta$ to a desired BVO interval for delivering cardiac resynchronization therapy, wherein the desired BVO interval is determined by a measurement of a cardiac function parameter.

In Example 19, the method of any one or more of Examples 14-18 optionally comprises: sensing an atrial event; measuring an intrinsic atrio-ventricular interval $AV_R$ using the sensed atrial event and the sensed right ventricular intrinsic activation; measuring an intrinsic atrio-ventricular interval $AV_L$ using the sensed atrial event and the sensed left ventricular intrinsic activation; and computing a second BVO interval as a function of the $AV_R$ and the $AV_L$.

In Example 20, the method of any one or more of Examples 14-19 optionally is performed such that $BVO = k_4(\Delta_{RL}) + k_5$, wherein $\Delta_{RL}$ is the difference between the $AV_R$ and the $AV_L$, wherein the coefficients $k_4$ and $k_5$ are derived from an analysis of clinical population data relating measured $\Delta_{RL}$ to a desired BVO interval for delivering cardiac resynchronization therapy, and wherein the desired BVO interval is determined by a measurement of a cardiac function parameter.

In Example 21, the method of any one or more of Examples 14-20 optionally is performed such that setting a BVO interval using at least one of the first BVO interval or the second BVO interval.

In Example 22, the method of any one or more of Examples 14-21 optionally is performed such that the setting the BVO interval includes as a function of the first BVO interval and the second BVO interval.

In Example 23, the method of any one or more of Examples 14-22 optionally is performed such that the setting the BVO interval includes as: $BVO = k_9(\beta) + k_{10}(AV_R) + k_{11}(AV_L) + k_{12}$, wherein the coefficients $k_9$, $k_{10}$, $k_{11}$, and $k_{12}$ are derived from an analysis of clinical population data relating measured $\beta$, $AV_R$, and $AV_L$ to a desired BVO interval for delivering cardiac resynchronization therapy, and wherein the desired BVO interval is determined by a measurement of a cardiac function parameter.

In Example 24, the method of any one or more of Examples 14-23 optionally is performed such that the setting the BVO interval includes as: $BVO = k_{13}(\beta) + k_{14}(\Delta_{RL}) + k_{15}$, wherein the coefficients $k_{13}$, $k_{14}$, and $k_{15}$ are derived from an analysis of clinical population data relating measured $\beta$ and $\Delta_{RL}$ to a desired BVO interval for delivering cardiac resynchronization therapy, and wherein the desired BVO interval is determined by a measurement of a cardiac function parameter.

In Example 25, the method of any one or more of Examples 14-24 optionally is performed such that setting the BVO interval includes selecting between the first BVO interval and the second BVO interval.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Generally, biventricular pacing includes pacing where energy is delivered to both the right and left ventricles. In certain examples, during biventricular pacing, the paces to right and left ventricles are delivered either simultaneously or substantially at the same time, with the interval between the paces termed the biventricular offset (BVO) interval (also sometimes referred to as the left ventricular offset (LVO) interval or ventricle-ventricle (VV) delay). In an example, the BVO can be computed or set to zero in order to pace both ventricles substantially at the same time, or the BVO interval can be computed or set to non-zero in order to pace the left and right ventricles sequentially.

The present inventors have recognized, among other things, that a first BVO interval can be established or adjusted by determining an earlier intrinsic activation and a later intrinsic activation of a right ventricle and a left ventricle, and computing the first BVO interval as a function of an interval from (1) a first pacing energy delivered to a ventricle corresponding to the later intrinsic activation and (2) a depolarization sensed in a ventricle having earlier intrinsic activation, wherein the depolarization was evoked in response to the pacing energy.

Figure 1:
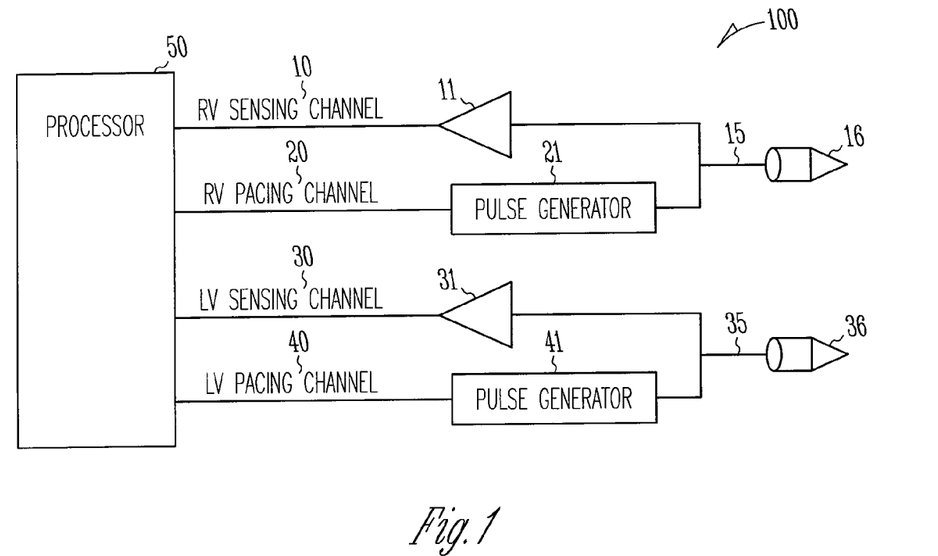
FIGS. 1, 2, and 3 illustrate generally examples of systems or portions of a system for delivering cardiac resynchronization therapy.

FIG. 1 illustrates generally an example of a system 100 for delivering cardiac resynchronization therapy. In an example, the system 100 can include a processor 50 having a right ventricular sensing channel 10, a right ventricular pacing channel 20, a left ventricular sensing channel 30, and a left ventricular pacing channel 40. In certain examples, the right ventricular sensing channel 10 can include a sense amplifier 11, the left ventricular sensing channel 30 can include a sense amplifier 31, the right ventricle pacing channel 20 can include a pulse generator 21, and the left ventricular pacing channel 40 can include a pulse generator 41. In other examples, the right ventricular sensing channel 10 or the right ventricular pacing channel 20 can be coupled to an electrode 16 disposed on a lead 15 or elsewhere, and the left ventricular sensing channel 30 or the left ventricular pacing channels 40 can be coupled to an electrode 36 disposed on a lead 35 or elsewhere.

In certain examples, the lead 15 can be configured to electrically couple the sense amplifier 11 or the pulse generator 21 to the electrode 16, which can be configured to be located in a right ventricle, such as in the septal region, the free wall region, or another region of the right ventricle. Similarly, the lead 35 can be configured to electrically couple the sense amplifier 31 or the pulse generator 41 to the electrode 36, which can be configured to be located in a left ventricle, such as in the septal region, the free wall region, or another region of the left ventricle.

In the example of FIG. 1, the processor 50 can be an implantable component, an external component, or a combination or permutation of an implantable processor and an external processor. In an example, if at least a portion of the processor 50 includes an external processor, then the processor 50 can be configured to be communicatively coupled (such as via telemetry, RF, or other communication protocol) with the remaining implantable components (such as the sense amplifier 11, 31, the pulse generator 21, 41, the lead 15, 35, or the electrode 16, 36). In an example, the implantable processor can be configured to have reduced or minimal functionality or power consumption. In certain examples, it can be advantageous for the processor 50 to include an external processor for computing complex operations, such as to compute a BVO interval. In other examples, the external processor can include an external device that can be either local or remote. In an example, the processor 50 can include a microcontroller, a microprocessor, a logic circuit, or other processor.

Figure 2:
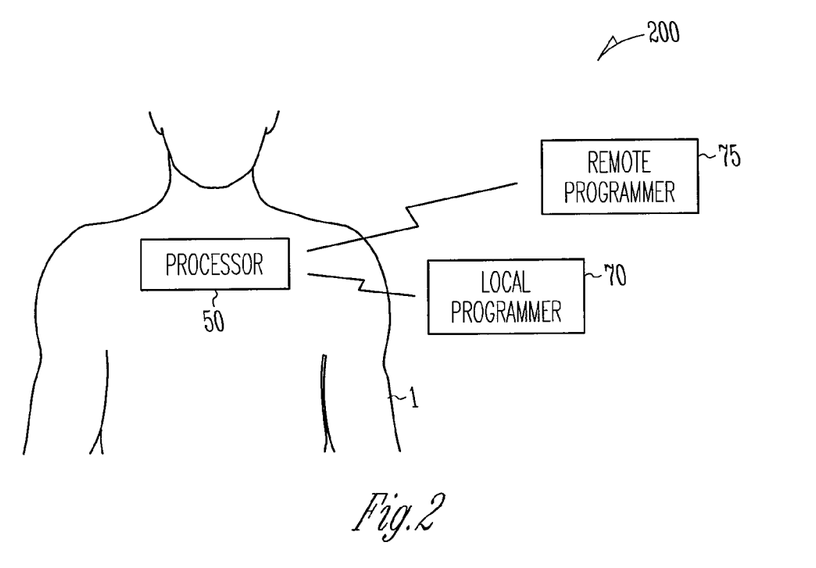

FIG. 2 illustrates generally an example of a portion of a system 200 including a processor 50 configured to be implanted in a subject 101. The system 200 can include at least one of a local programmer 70 or a remote programmer 75. Both the local programmer 70 and the remote programmer 75 are external components. In an example, the local programmer 70 can include a hand-held programmer or other programmer capable of being positioned in communication proximity to the processor 50. The proximity range between the processor 50 and the local programmer 70 can vary depending upon the type of data communication and is bound by the physical constraints of the communication type. In an example, the remote programmer 75 can include any programmer configured to communicate with the processor 50 either directly or indirectly (such as through another device, e.g., a router, the local programmer 70, etc.). In various examples, the remote programmer 75 can be configured to communicate with or store information from a plurality of implanted or external devices, and the remote programmer 75 can be configured to be located a long distance from the subject 101.

In an example, the local programmer 70 or the remote programmer 75 can be configured to send information to or receive information from the processor 50. The information can include programming information, subject data, device data, or other instructions, alerts, or other information. Further, the local programmer 70 or the remote programmer 75 can be configured to communicate the sent or received information to a user or physician, such as by sending an alert via email of the status of the subject 101 or the system components.

Figure 3:
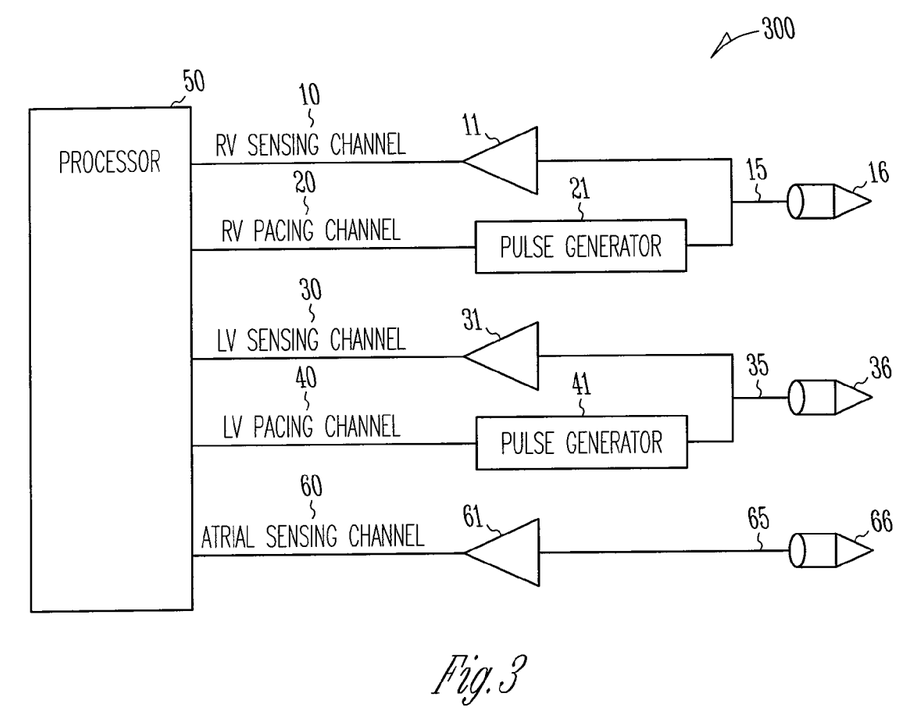

FIG. 3 illustrates generally an example of a system 300 for delivering cardiac resynchronization therapy. In an example, the system 300 can include a processor 50 having an atrial sensing channel 60. The atrial sensing channel 60 can include at least one of a right atrial sensing channel or a left atrial sensing channel. In certain examples, the atrial sensing channel 60 can include a sense amplifier 61, and the atrial sensing channel 60 can be coupled to a lead 65 having an electrode 66. The lead 65 can be configured to electrically couple the sense amplifier 61 to the electrode 66, which can be configured to be located in at least one of a right atrium or a left atrium of the subject 101.

Cardiac Resynchronization Therapy (CRT)

CRT can be used to improve a subject's cardiac pumping function by using pacing pulses to compensate for interventricular and/or intraventricular conduction deficits. CRT is sometimes delivered in an atrial-tracking or AV sequential mode and involves specification of BVO intervals, which can be used to result in the ventricles being synchronized during systole after being preloaded during atrial systole. In this way, both desired interventricular synchrony and desired atrioventricular synchrony are achieved. In subjects with intact and normally functioning AV conduction pathways, the non-pre-excited ventricle can be paced, if at all, close to the time at which that ventricle is intrinsically activated, such as in order to achieve desired preloading. In subjects with normal AV conduction, the desired BVO interval can be thus related to both the intrinsic atrio-ventricular interval and the amount of pre-excitation needed for one ventricle relative to the other (e.g., the extent of the ventricular conduction deficit).

In an example, CRT can be used to treat left or right ventricular dysfunction brought about by parts of the left ventricle or the right ventricle contracting later than normal during an intrinsic cardiac cycle. In an example, biventricular pacing can treat CRT by pre-exciting the left ventricle with a first pace delivered to the left ventricle followed by a pace to the right ventricle at the BVO interval. In another example, the right ventricle can pre-excited with a first pace delivered to the right ventricle followed by a pace to the left ventricle at the BVO interval. In an example, the left ventricle electrode can excite the left ventricular free wall, while the right ventricle electrode can excite the ventricular septum. In other examples, the left ventricle electrode can excite the ventricular septum, while the right ventricle can excite the left ventricular free wall. It may be desirable to effect simultaneous contraction of the left or right ventricular free wall and septum.

Computing the Biventricular Offset (BVO) Interval

In an example, a BVO interval can be specified for a subject using clinical hemodynamic testing performed after implantation where one or more parameters are varied as cardiac function is assessed. For example, a subject may be given resynchronization stimulation while varying one or more pre-excitation timing parameters in order to determine the parameter values that result in maximum cardiac performance, such as determined by measuring a parameter reflective of cardiac function, such as maximum left ventricular pressure change (dP/dt), arterial pulse pressure, or measurements of cardiac output. Determining desired pacing parameters for an individual subject by clinical hemodynamic testing, however, can be difficult and costly. The present inventors have recognized, among other things, that the desired pacing parameters can be determined from measurements of paced or intrinsic conduction parameters, which reflect how excitation is conducted within the subject's heart during paced or intrinsic beats.

From clinical hemodynamic testing performed on a population of subjects with intact AV pathways to determine the desired values of the BVO interval, it can be determined that there is a correlation between the desired BVO interval for a particular subject and that subject's measured conduction delay between the right and left ventricles.

In order to pre-derive certain specified coefficients (explained below) for later programming into the system or for use by a clinician, clinical population data can be obtained that relates particular values of the measured intrinsic conduction parameters to a desired value of the pre-excitation timing parameter, such as can be determined by concurrent measurement of another parameter reflective of cardiac function (e.g., maximum dP/dt or minimum atrial rate). An analysis can then be performed to derive values of the specified coefficients used in a formula for setting a pre-excitation timing parameter. In certain examples, the specified coefficients include regression coefficients, as explained below.

Figure 4:
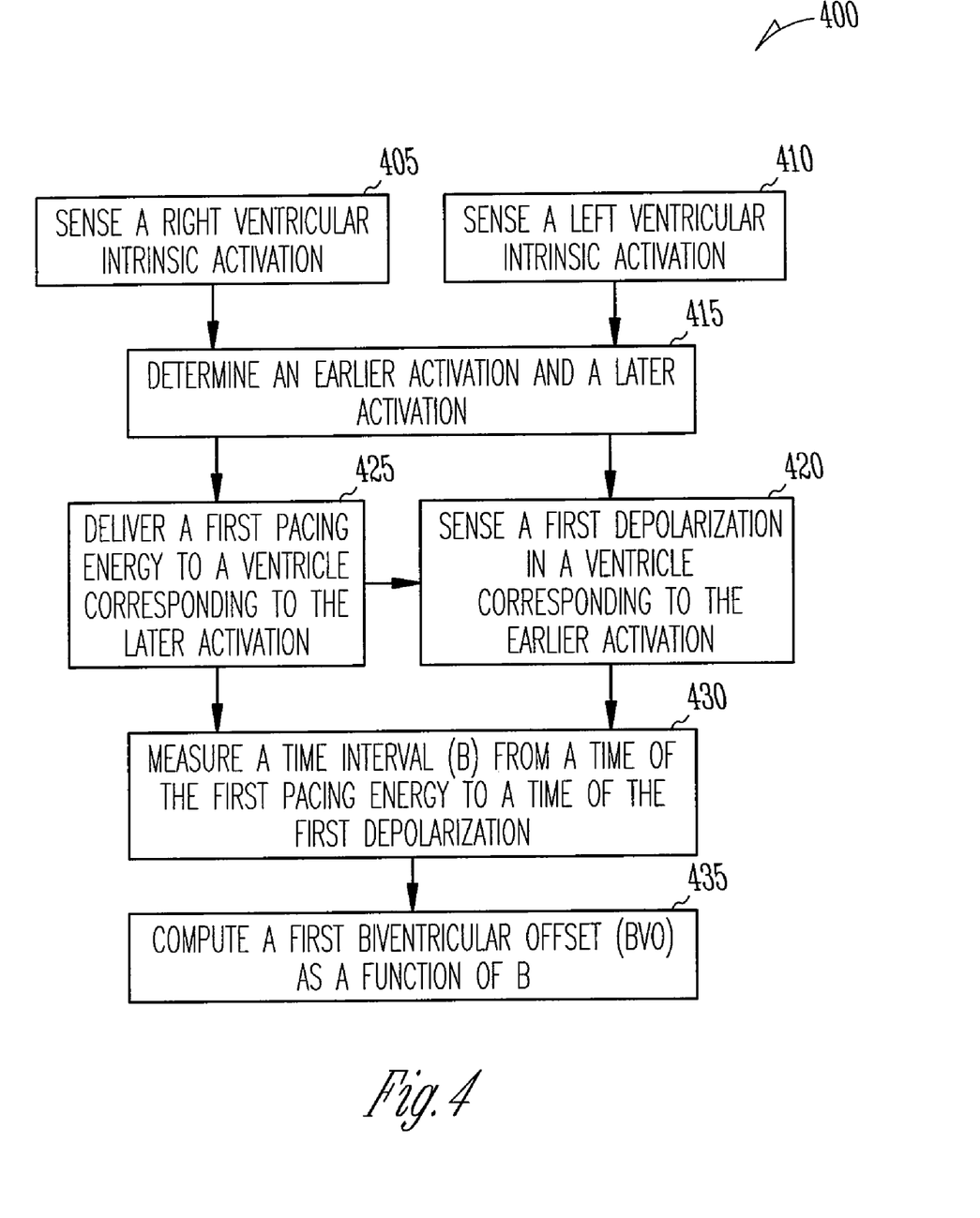
FIGS. 4 and 5 illustrate generally examples of methods or portions of a method for computing a first or second biventricular offset (BVO).

FIG. 4 illustrates generally an example of a method 400 including computing a first BVO interval. Generally, for a particular cardiac cycle, most subjects exhibit a later intrinsic activation in the left ventricle and an earlier intrinsic activation in the right ventricle. Others, however, exhibit a later intrinsic activation in the right ventricle and an earlier intrinsic activation in the left ventricle. As such, the sequence or order of intrinsic ventricular activations in the left and right ventricle can be determined in order to more accurately calculate a physiologically appropriate BVO interval.

At 405, a right ventricular intrinsic activation can be sensed. In an example, the right ventricular intrinsic activation can be sensed at a first location of the right ventricle (such as the septal region or the free wall region of the right ventricle). In an example, the right ventricular intrinsic activation can be sensed using the right ventricular sensing channel 10, the lead 15, the electrode 16, and the sense amplifier 11.

At 410, a left ventricular intrinsic activation can be sensed. In an example, the left ventricular intrinsic activation can be sensed at a first location in the left ventricle (such as the free wall region or the septal region of the left ventricle). In an example, the left ventricular intrinsic activation can be sensed using the left ventricular sensing channel 30, the lead 35, the electrode 36, and the sense amplifier 31.

At 415, an earlier activation and a later activation can be determined, as between the right and left ventricles during the same cardiac cycle. In an example, the earlier and later activation are determined during a first cardiac cycle using information about the sensed right and left ventricular intrinsic activations. In various examples, different methods can be used to determine the earlier and later activation. For example, a processor can monitor a channel receiving left ventricular activation data and right ventricular activation data for the first intrinsic activation following an atrial event and record the corresponding ventricle as the determined earlier activation. In that case, the other ventricle could automatically be deemed as having the later activation. In other examples, a processor can be configured to compare sensed intervals from an atrial event (or other common marker) to the right and left ventricle intrinsic activations and determine the earlier activating ventricle from the comparison. In an example, the earlier and later activation can be determined using the processor 50.

At 420, a first pacing energy can be delivered to a ventricle corresponding to the later activation during a second cardiac cycle. The first pacing energy delivered to the ventricle corresponding to the later activation can include a pacing energy reasonably expected to induce a depolarization in the ventricle corresponding to the earlier activation (e.g., if the ventricle corresponding to the later activation was determined to be the right ventricle, then the first pacing energy can be delivered to the right ventricle and can be such that it is reasonably expected to induce a depolarization in the left ventricle). In an example, the first pacing energy can be delivered using at least one of the right ventricular pacing channel 20 or the left ventricular pacing channel 40.

In an example, at 420, the first pacing energy can be delivered at a desired AVD interval after an atrial event. In an example, an atrial event (an atrial pace or a atrial sense) can trigger the beginning of an atrio-ventricular delay (AVD) interval. The AVD interval can be computed, varied, set, or otherwise modulated or changed, such as disclosed in the commonly assigned Ding et al. U.S. Pat. No. 7,013,176 entitled "METHOD AND SYSTEM FOR SETTING CARDIAC RESYNCHRONIZATION THERAPY PARAMETERS;" U.S. Pat. No. 7,123,960 entitled "METHOD AND SYSTEM FOR DELIVERING CARDIAC RESYNCHRONIZATION THERAPY WITH VARIABLE ATRIO-VENTRICULAR DELAY;" U.S. Pat. No. 7,203,540 entitled "METHOD AND SYSTEM FOR SETTING CARDIAC RESYNCHRONIZATION THERAPY PARAMETERS;" U.S. Ser. No. 11/206,394 entitled "METHOD AND SYSTEM FOR DELIVERING CARDIAC RESYNCHRONIZATION THERAPY WITH VARIABLE ATRIO-VENTRICULAR DELAY;" and U.S. patent Ser. No. 11/681,244 entitled "METHOD AND SYSTEM FOR SETTING CARDIAC RESYNCHRONIZATION THERAPY PARAMETERS;"

each of which are hereby incorporated by reference in their entirety, including their disclosure of setting an AVD interval.

At 425, a first depolarization can be sensed in a ventricle corresponding to the earlier activation. In this example, the first depolarization can include a depolarization induced by the delivery of the first pacing energy. In an example, the first depolarization can be sensed using at least one of the right ventricular sensing channel 10 or the left ventricular sensing channel 30.

At 430, a first time interval ($\beta$) from a time of the first pacing energy to a time of the first depolarization is measured. In certain examples, the time of the first pacing energy can include the time at which the processor 50 (or other component or user) issues the instruction to deliver the first pacing energy, or the time of the first pacing energy can include another portion of the first pacing energy. In another example, the time of the first depolarization can include the time at which the depolarization occurs, the time when the first depolarization starts, or other time substantially related to the first depolarization.

At 435, a first BVO interval can be computed as a function of $\beta$. In an example, the first BVO interval can be computed as a ratio of $\beta$:

$$BVO = k_1(\beta) \quad \text{(Eq. 1)}$$

wherein $0 \leq |k_1| \leq 1$. In an example, $k_1$ can be defined as a specific number within that range (e.g., 0.5), or within a narrower range (e.g., $0.25 \leq |k_1| \leq 0.75$, or $0.4 \leq |k_1| \leq 0.6$).

In other examples, at 435, the first BVO interval can be computed as:

$$BVO = k_2(\beta) + k_3 \quad \text{(Eq. 2)}$$

wherein the coefficients $k_2$ and $k_3$ can be derived from an analysis of clinical population data relating measured $\beta$ to a desired BVO interval for delivering cardiac resynchronization therapy, wherein the desired BVO interval is determined by a measurement of a cardiac function parameter. In certain examples, such cardiac function parameters can include a maximum left ventricular pressure change (dP/dt), arterial pulse pressure, or measurements of cardiac output.

Figure 5:
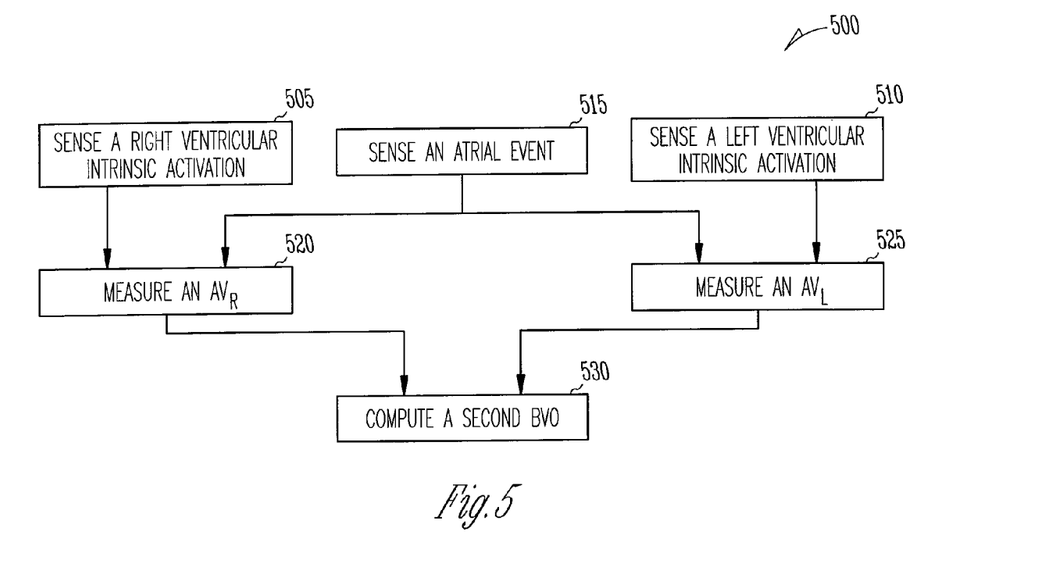

FIG. 5 illustrates generally an example of a method 500 for computing a second biventricular offset (BVO) interval.

At 505, a right ventricular intrinsic activation can be sensed. In an example, the right ventricular intrinsic activation can be sensed at a first location of the right ventricle (such as the septal region or the free wall region of the right ventricle). In an example, the right ventricular intrinsic activation can be sensed using the right ventricular sensing channel 10, the lead 15, the electrode 16, and the sense amplifier 11.

At 510, a left ventricular intrinsic activation can be sensed. In an example, the left ventricular intrinsic activation can be sensed at a first location in the left ventricle (such as the free wall region or the septal region of the left ventricle). In an example, the left ventricular intrinsic activation can be sensed using the left ventricular sensing channel 30, the lead 35, the electrode 36, and the sense amplifier 31.

At 515, an atrial event is sensed. The atrial event can include a right atrial event or a left atrial event. In an example, the atrial event can be sensed using the atrial sensing channel 60, the lead 65, the electrode 66, and the sense amplifier 61.

At 520, an intrinsic atrio-ventricular interval $AV_R$ can be measured using the sensed atrial event and the sensed right ventricular intrinsic activation. At 525, an intrinsic atrio-ventricular interval $AV_L$ can be measured using the sensed atrial event and the sensed left ventricular intrinsic activation. In an example, the $AV_R$ and the $AV_L$ can be measured using the processor 50.

At 530, a second BVO interval can be computed as a function of the $AV_R$ and the $AV_L$. In an example, the second BVO can be computed as:

$$BVO = k_4(AV_R) + k_5(AV_L) + k_6 \quad \text{(Eq. 3)}$$

wherein the coefficients $k_4$, $k_5$, and $k_6$ can be derived from an analysis of clinical population data relating measured $AV_R$ and $AV_L$ to a desired BVO interval for delivering cardiac resynchronization therapy, and wherein the desired BVO interval can be determined by a measurement of a cardiac function parameter.

In an example, the second BVO can be computed as:

$$BVO = k_7(\Delta_{RL}) + k_8 \quad \text{(Eq. 4)}$$

wherein $\Delta_{RL}$ is the difference between the $AV_R$ and the $AV_L$, wherein the coefficients $k_7$ and $k_8$ can be derived from an analysis of clinical population data relating measured $\Delta_{RL}$ to a desired BVO interval for delivering cardiac resynchronization therapy, and wherein the desired BVO interval can be determined by a measurement of a cardiac function parameter.

Figure 6:
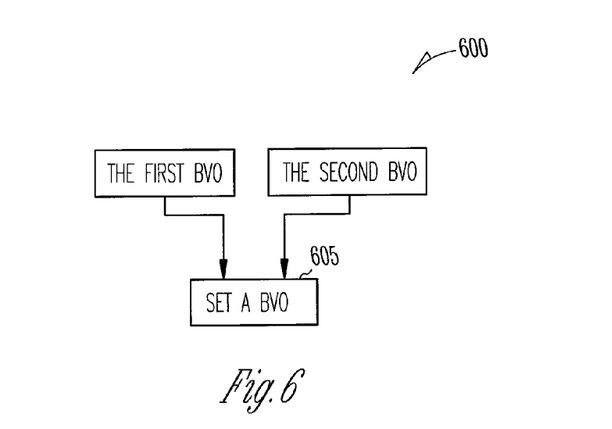
FIG. 6 illustrates generally an example of a portion of a method for setting a BVO.

FIG. 6 illustrates generally an example of a portion of a method 600 for setting a BVO interval using at least one of the first BVO or the second BVO. In an example, the BVO interval can be set using the processor 50.

In an example, the BVO interval can be set as a function of the first BVO and the second BVO. In an example, the BVO interval can be set as:

$$BVO = k_9(\beta) + k_{10}(AV_R) + k_{11}(AV_L) + k_{12} \quad \text{(Eq. 5)}$$

wherein the coefficients $k_9$, $k_{10}$, $k_{11}$, and $k_{12}$ can be derived from an analysis of clinical population data relating measured $\beta$, $AV_R$, and $AV_L$ to a desired BVO interval for delivering cardiac resynchronization therapy, and wherein the desired BVO interval can be determined by a measurement of a cardiac function parameter.

In another example, the BVO interval can be set as:

$$BVO = k_{13}(\beta) + k_{14}(\Delta_{RL}) + k_{15} \quad \text{(Eq. 6)}$$

wherein the coefficients $k_{13}$, $k_{14}$, and $k_{15}$ can be derived from an analysis of clinical population data relating measured $\beta$ and $\Delta_{RL}$ to a desired BVO interval for delivering cardiac resynchronization therapy, and wherein the desired BVO interval can be determined by a measurement of a cardiac function parameter.

In other examples, the BVO interval can be selected from the first BVO and the second BVO, such as selected by a physician or other user or selected using threshold amounts (e.g., use the BVO interval when the first BVO interval is within a certain threshold, etc.).

The techniques for setting resynchronization pacing parameters as described above, as well as others to be described below, can be implemented in a number of different ways. In one implementation, a system for setting the pacing parameters includes an external programmer. In an example, one or more intrinsic conduction parameters, as measured from electrogram signals generated by the sensing channels of an implantable cardiac resynchronization device during intrinsic beats, are transmitted to the external programmer via a wireless telemetry link. The measured intrinsic conduction parameters can represent averages of values obtained during a specified number of intrinsic beats. The external programmer then computes a pre-excitation timing parameter such as the BVO interval in accordance with a formula that equates a desired value of the pre-excitation timing parameter to a linear sum of the measured intrinsic conduction parameters multiplied by specified coefficients. In an automated system, the external programmer then automatically programs the implantable device with the computed desired parameter values, while in a semi-automated system the external programmer presents the computed desired values to a clinician in the form of a recommendation. An automated system can also be made up of the implantable device alone which collects intrinsic conduction data, computes the desired parameter values, and then sets the parameters accordingly. In another embodiment, which may be referred to as a manual system, the external programmer presents the collected intrinsic conduction data to a clinician who then programs the implantable device with parameters computed from the intrinsic conduction data by, for example, using a printed lookup table and procedure.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system, comprising:
   a right ventricular sensing channel configured to sense a right ventricular intrinsic activation;
   a left ventricular sensing channel configured to sense a left ventricular intrinsic activation;
   a right ventricular pacing channel configured to deliver a pacing energy to a right ventricle;
   a left ventricular pacing channel configured to deliver a pacing energy to a left ventricle; and
   an implantable or external processor, communicatively coupled to the right and left ventricular sensing and pacing channels, wherein the processor is configured to:
   determine an earlier activation and a later activation of the right ventricle and the left ventricle intrinsic activations during a first cardiac cycle using information about the sensed right and left ventricular intrinsic activations;
   trigger a first pacing energy to a ventricle corresponding to the later activation during a second cardiac cycle;
   receive an indication of a first depolarization in a ventricle corresponding to the earlier activation, the first depolarization being evoked in response to the first pacing energy;
   measure a first interval ($\beta$) from a time of the first pacing energy to a time of the first depolarization; and
   compute a first biventricular pacing interval between left and right ventricular paces, a first biventricular offset (BVO) interval, as a function of the first interval $\beta$.

2. The system of claim 1, wherein the processor is configured to trigger the first pacing energy at a specified atrio-ventricular delay (AVD) after a right atrial event.

3. The system of claim 1, wherein the processor is configured to compute the first BVO interval as:

$$BVO=k_1(\beta)$$

wherein $0 \leq |k_1| \leq 1$.

4. The system of claim 3, wherein $k_1$ is 0.5.

5. The system of claim 1, wherein the processor is configured to compute the first BVO interval as:

$$BVO=k_2(\beta)+k_3$$

wherein the coefficients $k_2$ and $k_3$ are derived from an analysis of clinical population data relating measured $\beta$ to a desired BVO interval for delivering cardiac resynchronization therapy, wherein the desired BVO interval is determined by a measurement of a cardiac function parameter.

6. The system of claim 1, including:
   an atrial sensing channel configured to sense an atrial event; and
   wherein the processor is configured to measure an intrinsic atrio-ventricular interval $AV_R$ using the sensed atrial event and the sensed right ventricular intrinsic activation, to measure an intrinsic atrio-ventricular interval $AV_L$ using the sensed atrial event and the sensed left ventricular intrinsic activation, and to compute a second BVO interval as a function of the $AV_R$ and the $AV_L$.

7. The system of claim 6, wherein the processor is configured to compute the second BVO interval as:

$$BVO=k_4(AV_R)+k_5(AV_L)+k_6$$

wherein the coefficients $k_4$, $k_5$, and $k_6$ are derived from an analysis of clinical population data relating measured $AV_R$ and $AV_L$ to a desired BVO interval for delivering cardiac resynchronization therapy, and wherein the desired BVO interval is determined by a measurement of a cardiac function parameter.

8. The system of claim 6, wherein the processor is configured to compute the second BVO interval as:

$$BVO = k_7(\Delta_{RL}) + k_8$$

wherein $\Delta_{RL}$ is the difference between the $AV_R$ and the $AV_L$, wherein the coefficients $k_7$ and $k_8$ are derived from an analysis of clinical population data relating measured $\Delta_{RL}$ to a desired BVO interval for delivering cardiac resynchronization therapy, and wherein the desired BVO interval is determined by a measurement of a cardiac function parameter.

9. The system of claim 6, wherein the processor is configured to set a BVO interval using at least one of the first BVO interval or the second BVO interval.

10. The system of claim 9, wherein the processor is configured to set a BVO interval as a function of the first BVO and the second BVO.

11. The system of claim 10, wherein the processor is configured to set the BVO interval as:

$$BVO = k_9(\beta) + k_{10}(AV_R) + k_{11}(AV_L) + k_{12}$$

wherein the coefficients $k_9$, $k_{10}$, $k_{11}$, and $k_{12}$ are derived from an analysis of clinical population data relating measured $\beta$, $AV_R$, and $AV_L$, to a desired BVO interval for delivering cardiac resynchronization therapy, and wherein the desired BVO interval is determined by a measurement of a cardiac function parameter.

12. The system of claim 10, wherein the processor is configured to set the BVO interval as:

$$BVO = k_{13}(\beta) + k_{14}(\Delta_{RL}) + k_{15}$$

wherein $\Delta_{RL}$ is the difference between the $AV_R$ and the $AV_L$, wherein the coefficients $k_{13}$, $k_{14}$, and $k_{15}$ are derived from an analysis of clinical population data relating measured $\beta$ and $\Delta_{RL}$ to a desired BVO interval for delivering cardiac resynchronization therapy, and wherein the desired BVO interval is determined by a measurement of a cardiac function parameter.

13. The system of claim 7, wherein the processor is configured to set the BVO interval by selecting between the first BVO interval and the second BVO interval.

14. A method for setting desired pacing parameters for delivering cardiac resynchronization therapy to a subject, comprising:
   sensing a right ventricular intrinsic activation;
   sensing a left ventricular intrinsic activation;
   determining an earlier activation and a later activation of the right ventricle and the left ventricle intrinsic activations during a first cardiac cycle using information about the sensed right and left ventricular intrinsic activations;
   delivering a first pacing energy to a ventricle corresponding to the later activation during a second cardiac cycle;
   sensing a first depolarization in a ventricle corresponding to the earlier activation, the first depolarization being evoked in response to the first pacing energy;
   measuring a first interval ($\beta$) from a time of the first pacing energy to a time of the first depolarization; and
   computing a first biventricular pacing interval between left and right ventricular paces, a first biventricular offset (BVO) interval, as a function of the first interval $\beta$.

15. The method of claim 14, wherein the delivering the first pacing energy includes delivering at a predetermined desired atrioventricular delay (AVD) after a right atrial event.

16. The method of claim 14, wherein the computing the first BVO interval includes as:

$$BVO = k_1(\beta)$$

wherein $0 \leq |k_1| \leq 1$.

17. The method of claim 16, wherein $k_1$ is 0.5.

18. The method of claim 14, wherein the computing the first BVO interval includes as:

$$BVO = k_2(\beta) + k_3$$

wherein the coefficients $k_2$ and $k_3$ are derived from an analysis of clinical population data relating measured $\beta$ to a desired BVO interval for delivering cardiac resynchronization therapy, wherein the desired BVO interval is determined by a measurement of a cardiac function parameter.

19. The method of claim 14, including:
   sensing an atrial event;
   measuring an intrinsic atrioventricular interval $AV_R$ using the sensed atrial event and the sensed right ventricular intrinsic activation;
   measuring an intrinsic atrio-ventricular interval $AV_L$ using the sensed atrial event and the sensed left ventricular intrinsic activation; and
   computing a second BVO interval as a function of the $AV_R$ and the $AV_L$.

20. The method of claim 19, wherein the computing the second BVO interval includes as:

$$BVO = k_4(\Delta_{RL}) + k_5$$

wherein $\Delta_{RL}$ is the difference between the $AV_E$, and the $AV_L$, wherein the coefficients $k_4$ and $k_5$ are derived from an analysis of clinical population data relating measured $\Delta_{RL}$ to a desired BVO interval for delivering cardiac resynchronization therapy, and wherein the desired BVO interval is determined by a measurement of a cardiac function parameter.

21. The method of claim 19, including setting a BVO interval using at least one of the first BVO interval or the second BVO interval.

22. The method of claim 21, wherein the setting the BVO interval includes as a function of the first BVO interval and the second BVO interval.

23. The method of claim 22, wherein the setting the BVO interval includes as:

$$BVO = k_9(\beta) + k_{10}(AV_R) + k_{11}(AV_L) + k_{12}$$

wherein the coefficients $k_9$, $k_{10}$, $k_{11}$, and $k_{12}$ are derived from an analysis of clinical population data relating measured $\beta$, $AV_R$, and $AV_L$ to a desired BVO interval for delivering cardiac resynchronization therapy, and wherein the desired BVO interval is determined by a measurement of a cardiac function parameter.

24. The system of claim 22, wherein the setting the BVO interval includes as:

$$BVO = k_{13}(\beta) + k_{14}(\Delta_{RL}) + k_{15}$$

wherein $\Delta_{RL}$ is the difference between the $AV_R$ and the $AV_L$, wherein the coefficients $k_{13}$, $k_{14}$, and $k_{15}$ are derived from an analysis of clinical population data relating measured $\beta$ and $\Delta_{RL}$ to a desired BVO interval for delivering cardiac resynchronization therapy, and wherein the desired BVO interval is determined by a measurement of a cardiac function parameter.

25. The method of claim 21, wherein setting the BVO interval includes selecting between the first BVO interval and the second BVO interval.

* * * * *

UNITED STATES PATENT AND TRADEMARK OFFICE
CERTIFICATE OF CORRECTION

PATENT NO. : 8,271,084 B2  
APPLICATION NO. : 12/259055  
DATED : September 18, 2012  
INVENTOR(S) : Yu et al.

Page 1 of 1

It is certified that error appears in the above-identified patent and that said Letters Patent is hereby corrected as shown below:

In column 13, line 64 (Approx.), in claim 15, delete "atrioventricular" and insert --atrio-ventricular--, therefor In column 14, line 16 (Approx.), in claim 19, delete "atrioventricular" and insert --atrio-ventricular--, therefor In column 14, line 28, in claim 20, delete "$AV_E$" and insert --$AV_R$--, therefor Signed and Sealed this
Twenty-seventh Day of November, 2012

David J. Kappos
*Director of the United States Patent and Trademark Office*